United States Patent [19]
Tu et al.

[11] Patent Number: 6,102,908
[45] Date of Patent: Aug. 15, 2000

[54] ROTATABLE APPARATUS HAVING ABLATION CAPABILITIES

[76] Inventors: Lily Chen Tu; Hosheng Tu, both of 2151 Palermo, Tustin, Calif. 92782

[21] Appl. No.: 09/225,079

[22] Filed: Jan. 4, 1999

[51] Int. Cl.⁷ .................................................. A61B 18/18
[52] U.S. Cl. ................................ 606/41; 606/194; 606/42
[58] Field of Search ........................... 606/27–31, 41, 606/42, 191, 194, 198; 604/96

[56] References Cited

U.S. PATENT DOCUMENTS

| | | | |
|---|---|---|---|
| 4,799,479 | 1/1989 | Spears | 606/28 |
| 4,955,377 | 9/1990 | Lennox et al. | 606/27 |
| 5,151,100 | 9/1992 | Abele et al. | 606/28 |
| 5,178,618 | 1/1993 | Kandarpa | 606/28 |
| 5,292,321 | 3/1994 | Lee | 606/28 |
| 5,685,847 | 11/1997 | Barry | 604/96 |
| 5,921,954 | 7/1999 | Mohr, Jr. et al. | 604/53 |
| 6,017,324 | 1/2000 | Tu et al. | 604/962 |

*Primary Examiner*—Michael Peffley

[57] ABSTRACT

An ablation apparatus system for treating tissues or obstructions in vessels in the body includes a rotatable metallic member which is guided to the obstruction in a reduced diameter configuration, expanded and rotated to contact the tissue, optionally to remove the obstruction, and a RF current is applied to the tissue-contacting rotatable metallic member or the expanded stent for treating the tissues.

9 Claims, 4 Drawing Sheets

ROTATABLE APPARATUS HAVING ABLATION CAPABILITIES

FIELD OF THE INVENTION

The present invention generally relates to improved medical apparatus and methods for treating vascular tissues, and/or removing obstructions from vessels in the body, and more particularly, to such a rotatable metallic member which is guided to the obstruction in a reduced diameter configuration, expanded and rotated to treat the tissue, optionally removing the obstruction, and a RF current is applied to the tissue-contacting metallic member for treating the tissues. Still further the present invention relates to a combined stent implantation and RF current therapy having an expandable stent and RF current delivery system at the obstruction within the vessel for treating the tissues.

BACKGROUND OF THE INVENTION

An artery is one of the tube-shaped blood vessels that carry blood away from a heart to the body's tissues and organs. An artery is made up of an outer fibrous layer, a smooth muscle layer, connecting tissues and inner lining cells. If arterial walls become hardened due to the accumulation of fatty substances, then blood flow can be diminished. Hardening of the arteries, or loss of vessel elasticity, are termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through an artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream.

There are limitations, however, to this technique's application, depending on the extent of the disease, the blood flow through the artery, and the part of the anatomy and the particular vessels involved. Plaque build-up and/or severe re-stenosis recurs within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh or coil tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still suboptimal. The underlying fresh tissue or cells still pose as a precursor for vessel reclosures or angio-spasm.

Atherectomy is a relatively newer technique developed for opening the lumen of an occluded vessel, and like the balloon angioplasty technique, provides an alternative to the traditional coronary bypass surgery. Atherectomy involves physically breaking up the material that blocks or partially blocks the vessel. Several types of atherectomy devices have been developed. U.S. Pat. No. 4,445,509, No. 4,895,560, No. 4,966,604, No. 4,990,134, No. 5,217,474, No. 5,766,192, No. 5,779,722, No. 5,836,957, and No. 5,843,103 incorporated herein by reference, disclose a rotatable abrasive surface that is introduced into the obstructed vessel. At the obstruction the abrasive surface is rotated at a high rate of speed to abrade or cut away at the obstruction.

One major drawback with rotatable abrasive atherectomy devices is that they open up the plaque or the obstruction and expose the underlying collagen or damaged endothelium to the blood flow. Fresh collagen has pro-thrombotic and platelet-affinity properties that are part of body's healing process. Unless the collagen or the damaged endothelium is passivated or modulated, the chances for blood vessel clotting as well as restenosis exist. Moderate focal heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty, stenting, or atherectomy procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

Other situations may arise where it is advantageous or desirable to combine the benefits of a rotatable atherectomy-like procedure with means for expanding the constricted vessel and a RF current therapy for providing focal thermal energy to the treated tissue. With the prior art devices presently available, it is necessary that an angioplasty, atherectomy, or stenting be performed first; then RF energy is applied. There is an urgent clinical need to shorten and simplify the procedure by simultaneously performing rotating procedure comprising RF energy therapy as part of the angioplasty, atherectomy or stenting procedures.

A stent deployed within a vessel or a rotatable metallic device has excellent metal-to-tissue contact surface. It becomes an ideal medium for applying appropriate thermal energy to the tissue needed for treatment or modulation. A metallic stenting element or a rotatable metallic device is useful in this case to shrink and tighten the target tissue.

Therefore, there is a need for an improved medical apparatus having the capability to effectively contact the inner walls of a tubular vessel using radiofrequency energy to treat a vessel or other tissues, such as esophagus, larynx, uterus, urethra and the like.

SUMMARY OF THE INVENTION

In general, it is an object of the present invention to provide a method and an improved ablation apparatus system for generating heat, to treat the vascular vessels, or other tissues, such as intestine, colon, urethra, uterine tube, and the like. It is another object of the present invention to provide a method and an apparatus for monitoring the temperature of the ablated tissue, and to control the temperature by utilizing a temperature controller and/or algorithm. The location of the temperature sensor is preferably at close proximity of the metallic member of the ablation apparatus. It is still another object of this invention to provide a method and an apparatus for treating atherosclerosis, vascular walls, or tubular cellular tissues of a body by applying RF current to an expandable stent and consequently to the underlying tissues. It is still another object to provide an ablation apparatus system comprising a rotatable metallic member to contact the tissue while delivering RF energy to said tissue.

The rotatable metallic member consists of a metallic member attached to a rotating member of the ablation apparatus system. It may comprise a short length of ovaloid shaped coil that can be elongated, thereby decreasing its circumference as compared to its circumference in the normal wound configuration. Lengthening and rotating the coil reduce its circumference and facilitate its introduction to an obstructed area. The coil is then allowed to return to a normal wound configuration thereby increasing the overall circumference of the coil. The coil can be enlarged to a preselected circumference between the normal wound configuration and the elongated small circumference. After an obstruction is cleared, it is possible to decrease the circumference of the coil by elongation and rotation and easily withdraw the coil and associated catheter from the vessel.

The coil's circumference can be increased or decreased over a range by a remotely actuated means that will elongate or retract the coil as desired. In a preferred embodiment, the coil is tightly wound and multifiliar, preformed in an ovoid shape. The coil typically surrounds a means for facilitating introduction into the vessel where the obstruction is located, such as a catheter with a lumen for guide wire insertion. The coil is connected to a means for rotation. The rotating mechanism for a medical device may include a rotating motor, an expandable and contractible bellow, an inflatable balloon or the like, which mechanism is well known to one who is skilled in the art.

Briefly, heat is generated by supplying a suitable energy source to an apparatus, which is comprised of one electrode means, in contact with body tissues through an expandable stent or a rotatable metallic member. An "expandable stent" is defined in this invention as any metallic stenting element, in mesh form, coil form or other appropriate form, used to enlarge and maintain the enlarged tissues or vessels, wherein the expandable stent is also retractable or contractible so that the stent can be optionally withdrawn from the vessel. Examples include coronary stent, peripheral stent, uterine stent, temporary coil stent, and the like. A suitable energy source may consist of radiofrequency energy, microwave energy, ultrasonic energy, alternating current energy, or laser energy. The energy can be applied to the stent or the rotatable metallic member and consequently to the vessel walls, or cellular tissues. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using a high frequency current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In an optional embodiment, means for generating rotation or vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the apparatus vibrates. In the case of rotational operations, no weight is mounted. Instead, the motor shaft is coupled to the coil that is a short length of ovaloid shaped coil that can be elongated, thereby decreasing its circumference as compared to its circumference in the normal wound configuration. The coil tip is rotated at a desired speed during its passage through a constricted vessel or the enlarged vessel after angioplasty. Once the RF energy is properly delivered to the surrounding tissue, the coil is returned to its original smaller diameter and may be easily withdrawn from the vessel.

The rotating metallic member having RF capabilities may be combined with a balloon angioplasty device with but a single trip or entry into the occluded vessel, in situations where the use of such a combination is desired or required. The combined device thus saves time and expense, that is, the balloon angioplasty procedure followed by a separate RF therapy using a rotating metallic member of the ablation apparatus system.

In another embodiment, the rotating metallic member having RF capabilities may be combined with the benefit of a stent implantation procedure with a single trip or entry into the occluded vessel, in situations where the use of such a combination is desired or required. The combined device thus saves time and expense, that is, the stent implantation procedure followed by a separate RF therapy using a rotating metallic member of the ablation apparatus system to contact the stent for RF energy delivery to the underlying tissues through said stent.

The method and ablation apparatus system of the present invention has several significant advantages over other known systems or techniques to treat a constricted vessel or even an enlarged vessel. In particular, the apparatus system comprising the rotatable metallic member using RF energy as a heat source to treat the tissues results in a more efficient therapeutic effect, which is highly desirable in its intended application on the atherosclerosis or constricted vessels.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of the ablation apparatus system, comprising simultaneously applying radiofrequency energy and applying a rotational therapy to treat the atherosclerosis, vascular vessels, or other tubular cellular tissues of a patient.

Figure 1:
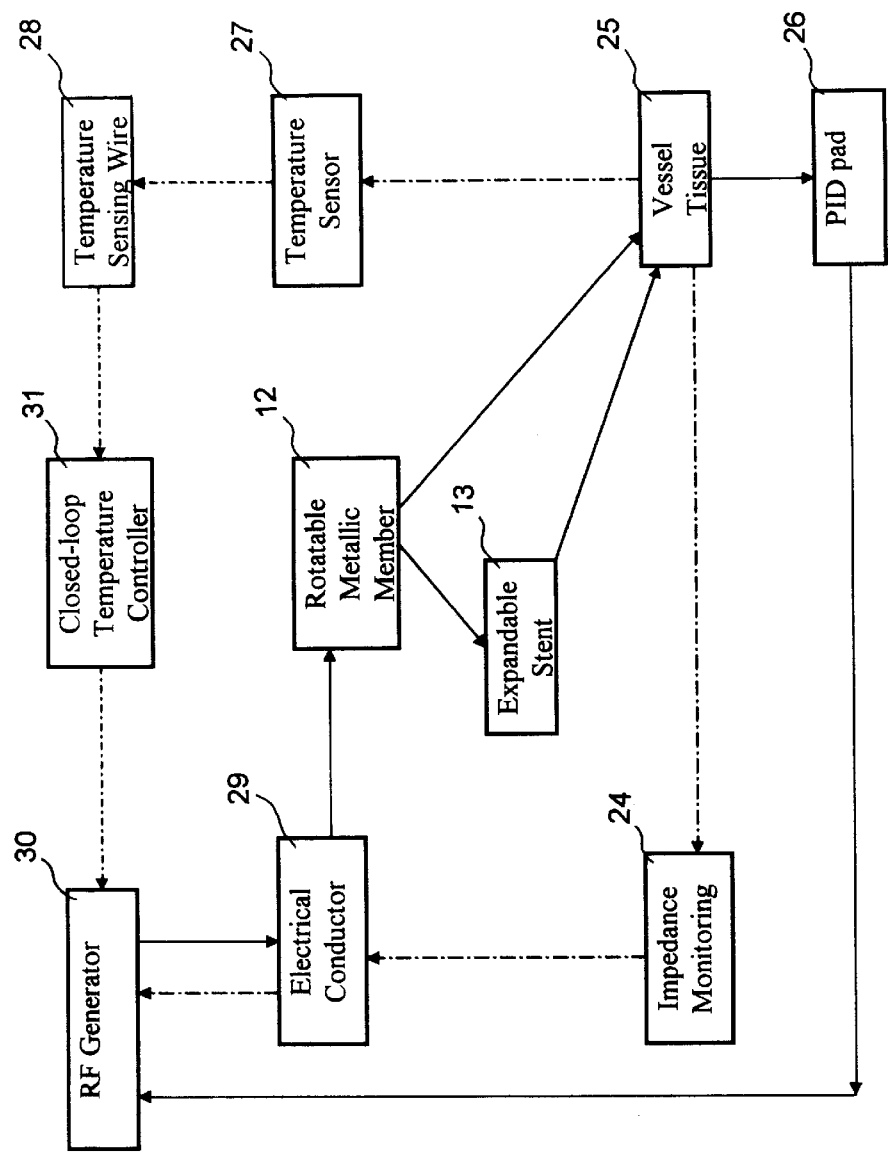
FIG. 1 is a schematic diagram of a RF treatment method in relation to the tissues of a vessel through a rotatable metallic member and/or an expandable stent in a patient.

FIG. 1 shows a schematic diagram of a RF treatment method in relation to the tissues through a rotatable metallic member in a patient. A RF generator 30 is connected to an expandable stent 13 or a rotatable metallic member 12 of an ablation apparatus 1 through an electrical conductor 29. In one embodiment, a rotatable metallic member 12 of an ablation apparatus 1 is to contact an expandable stent 13 when the apparatus is deployed. In another embodiment, the rotatable metallic member is to contact the tissue 25 directly. The stent is in close contact with the underlying tissue 25. A DIP (dispersive indifferent pad) type pad 26, that contacts the patient, is connected to the Indifferent Electrode Connector on the RF generator 30. Therefore, the RF energy delivery becomes effective when a close circuit from a RF generator 30 through a patient and returning to the RF generator is formed. Impedance 24 measured from the tissue contact is to ensure good tissue contact for ablation, otherwise the RF power is cutoff when the impedance is unreasonably off the acceptance value. A temperature sensor 27 is also used to measure the tissue temperature and is relayed through a temperature sensing wire 28 and a closed-loop temperature controller 31 for controlling the ablative energy delivered. Heat is controlled by the power of the RF energy delivered and by the delivery duration.

Figure 2:
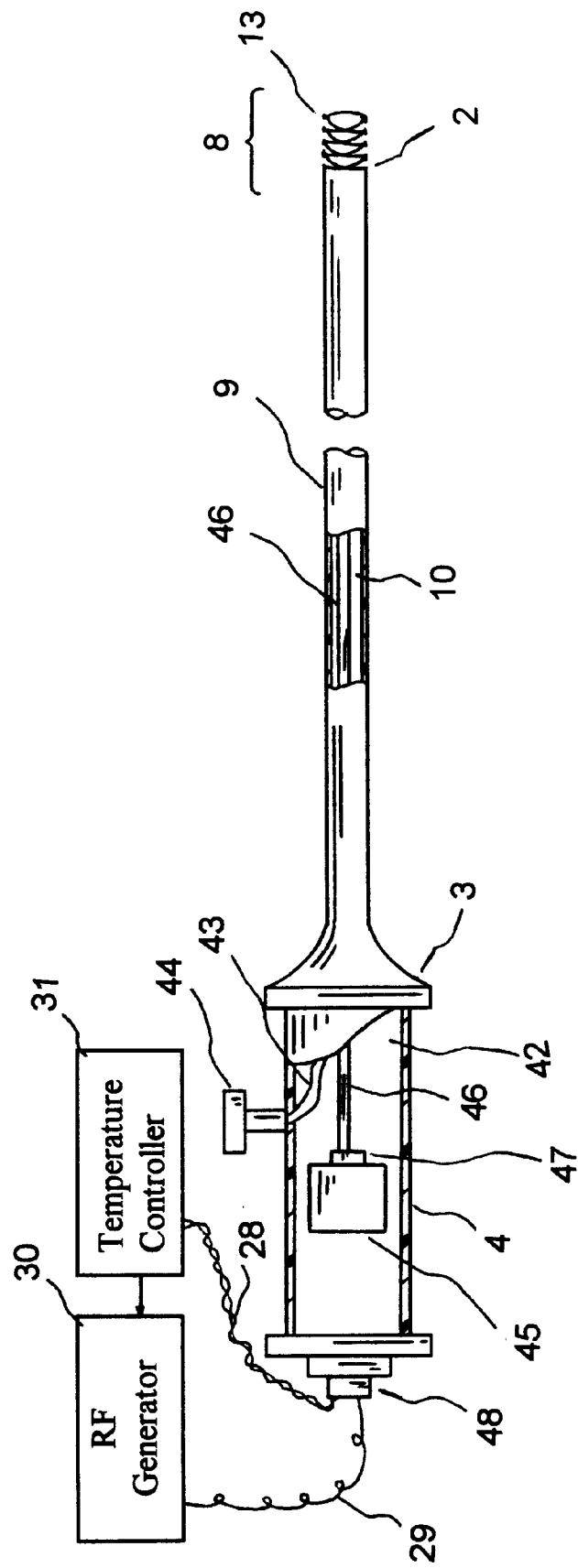
FIG. 2 is an overall view of a preferred ablation apparatus system having a rotatable metallic member and a RF generator, constructed in accordance to the principles of the present invention.

As shown in FIG. 2, the ablation apparatus system 1 in the form of an elongate tubular assembly comprises a tubular shaft 9 having a shaft distal section 8, a shaft distal end 2, a shaft proximal end 3, and at least one lumen 10 extending therebetween, wherein the at least one lumen has at least one opening 41 at the shaft distal end 2. A handle 4 is attached to the shaft proximal end 3, wherein the handle 4 has a cavity 42. An expandable stent 13 is disposed on the shaft distal section 8.

Figure 3:
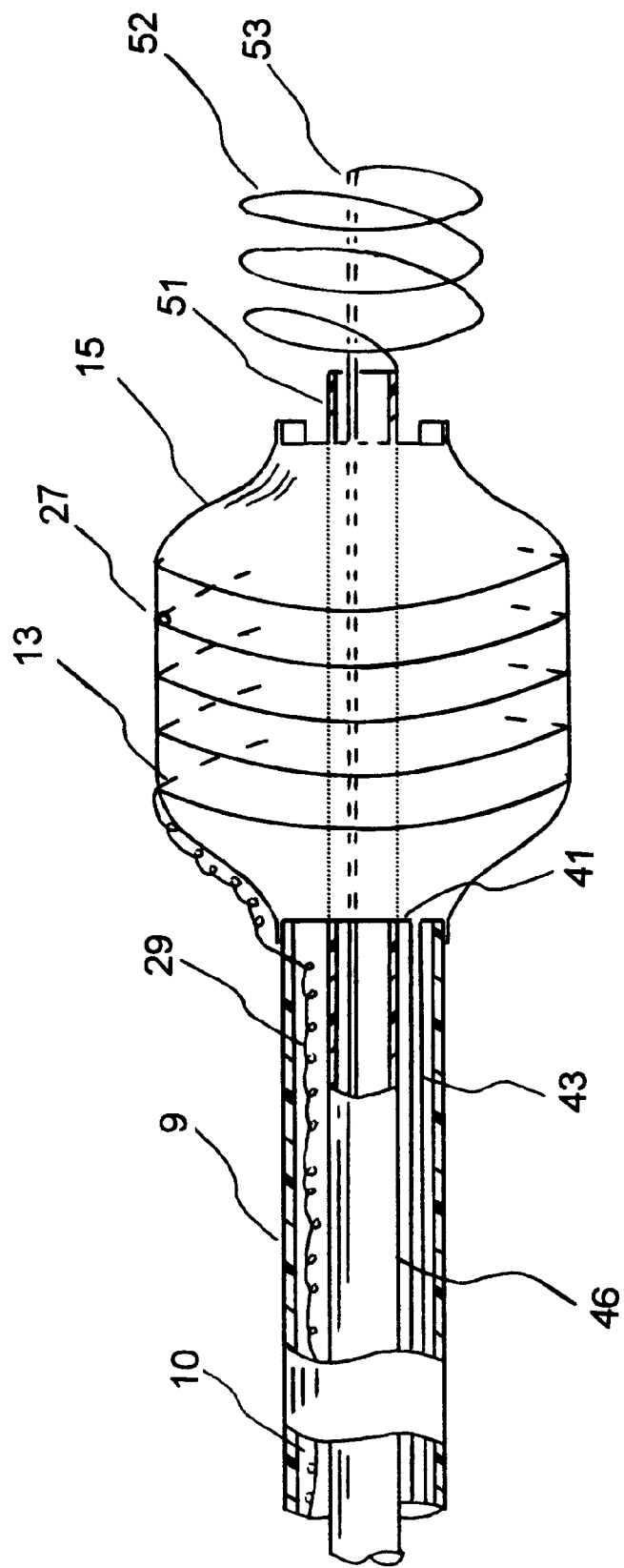
FIG. 3 is a side cross-sectional view of the distal end portion of the preferred apparatus, having an expandable stent and a rotatable metallic member positioned within a lumen of a tubular shaft, at a deployed state.

FIG. 3 shows a side cross-sectional view of the distal end portion of a preferred apparatus 1, having an expandable stent 13 and a rotatable metallic member 52 positioned within a lumen 10 of a tubular shaft 9, at a deployed state. The apparatus comprises an expandable member 15 disposed between the tubular shaft 9 and the expandable stent 13. The expandable member 15 has the capability of expanding beneath the expandable stent 13 to enlarge a circumference of the expandable stent 13. In a preferred embodiment, the expandable member 15 is an inflatable balloon, wherein the tubular shaft 9 includes a fluid passageway 43 and a fluid inlet port 44 for inflating the inflatable balloon 15. The expandable stent 13 is a self-expandable stent, a balloon-expandable stent or an expandable-retractable stent. The expandable stent may be made of a memory coil.

A RF current generator 30 is part of the ablation apparatus system 1, wherein an electrical conductor 29 is coupled from the RF generator 30 to the expandable stent 13 for delivering RF current to said expandable stent 13 for ablating the vessel. The RF current is preferably within the range of 50 kHz to 2,000 kHz.

The ablation apparatus system may further comprises a rotating member 51 extending through the tubular shaft 9 and being rotatable within the tubular shaft, wherein a metallic member 52 is attached to the rotating member 51. In a preferred embodiment, the metallic member 52 is helically wound. The metallic member 52 may comprise a short length of ovaloid shaped coil that can be elongated by pushing a supporting wire 53, thereby decreasing its circumference as compared to its circumference in the normal wound configuration. Lengthening and rotating the metallic member coil 52 by maneuvering the supporting wire 53 reduce its circumference and facilitate its introduction to an obstructed area. The coil is then allowed to return to a normal wound configuration thereby increasing the overall circumference of the coil.

In addition to the above-described components for the ablation apparatus system 1, there is a cavity 42 inside the handle 4, in which a motor 45 is located. The apparatus system further comprises means for generating rotation at the distal end portion of the apparatus system, wherein the means for generating rotation at the distal end portion comprises a motor 45 mounted in the cavity 42 of the handle 4. The rotating means comprises a rotatable motor shaft 47, an elongate connecting shaft 46 having a first end to which the rotating member 51 is connected, and a second end connected to the handle 4. When the motor shaft 47 rotates, the rotating member 51 of the apparatus system rotates.

In one embodiment, a battery means, which is located at the proximal end of the cavity 42 of the handle 4, is used to supply the energy to the motor 45. In an alternate embodiment, the motor 45 is powered by an alternate current (AC) through a power-input plug 48. In either case, the power supply is controlled by an on-off switch button located conveniently on the handle 4.

Figure 4:
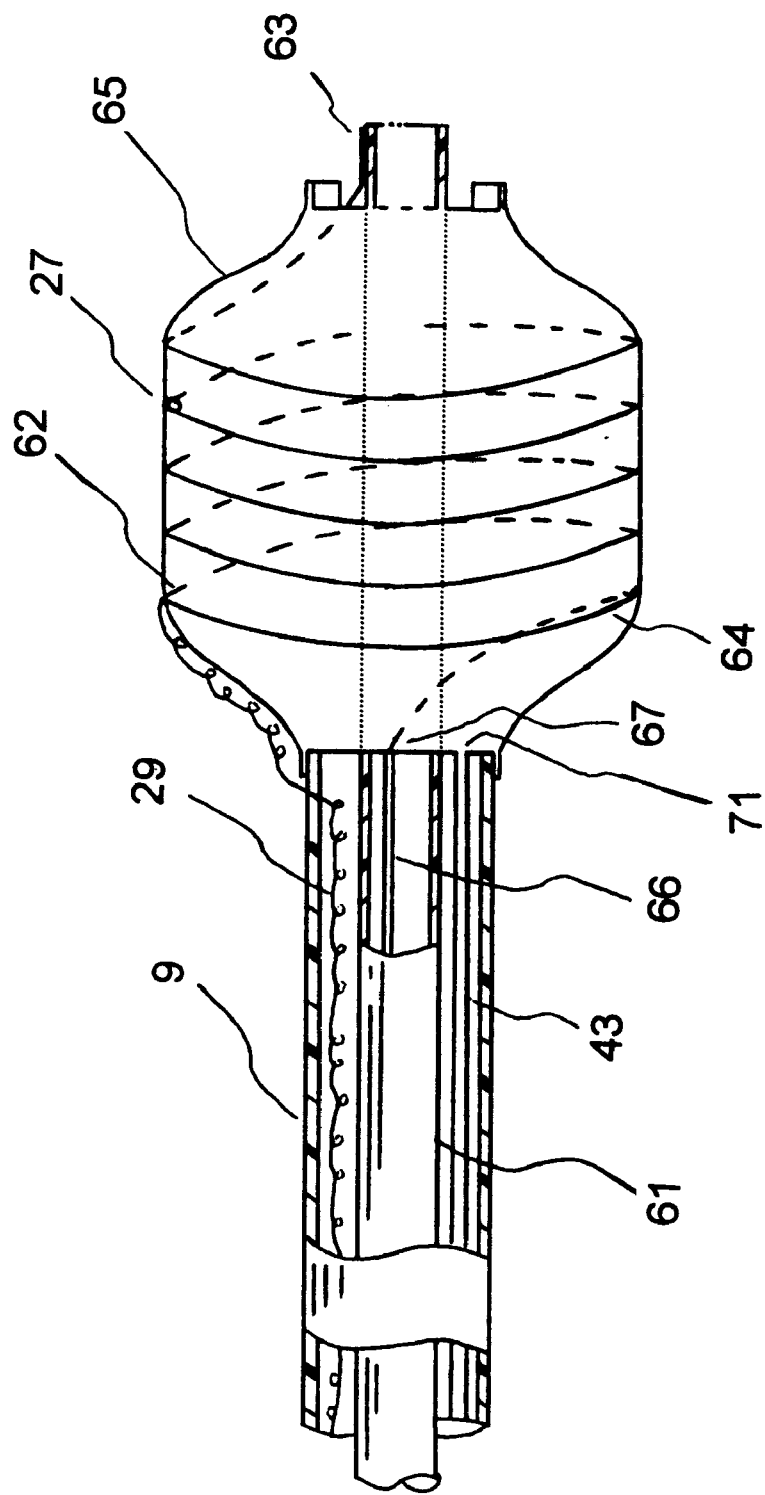
FIG. 4 is a side cross-sectional view of the distal end portion of an alternate apparatus, having an inflatable balloon, and a rotatable metallic member positioned within a lumen of a tubular shaft, at a deployed state.

FIG. 4 shows a side cross-sectional view of the distal end portion 8 of an alternate apparatus, having an inflatable balloon 65, and a rotatable metallic member positioned within a lumen of a tubular shaft, at a deployed state. An alternate ablation apparatus system for removing an obstruction and ablating a vessel, comprises a tubular shaft 9 and a hollow rotating member 61 rotatably disposed within the tubular shaft 9, wherein a metallic member 62 is disposed on an end 63 of the hollow rotating member 61 and forms an expandable circumferential outer surface 64. The expandable circumferential outer surface 64 has a metallic contacting surface covering at least a portion of said circumferential outer surface 64. A movable member 66 is disposed within the hollow rotating member 61, wherein the metallic member 62 has one end 67 coupled to said movable member 66 and another end 63 coupled to said hollow rotating member 61. An expandable member 65 is disposed beneath said metallic member 62 for expanding the expandable metallic member 62 into supporting engagement with the vessel.

In a preferred embodiment, the expandable member 65 is an inflatable balloon, wherein the tubular shaft 9 includes a fluid passageway 43, a fluid inlet port 44, and a fluid outlet port 71 for inflating the inflatable balloon 65. The expandable metallic member 62 is a self-expandable metallic member, a balloon-expandable metallic member or an expandable-retractable metallic member. The expandable metallic member 62 may be made of a memory coil. In a preferred embodiment, the metallic member 62 is helically wound. The metallic member 62 may comprise a short length of ovaloid shaped coil that can be elongated by pulling a movable member 66, thereby decreasing its circumference as compared to its circumference in the normal wound configuration. Lengthening and rotating the metallic member coil 62 by maneuvering the movable member 66 reduce its circumference and facilitate its introduction to an obstructed area. The coil is then allowed to return to a normal wound configuration thereby increasing the overall circumference of the coil.

A RF current generator 30 is part of the ablation apparatus system 1, wherein an electrical conductor 29 is coupled from the RF generator 30 to the expandable metallic member 62 for delivering RF current to said expandable metallic member 62 for ablating the vessel. The RF current is preferably within the range of 50 kHz to 2,000 kHz.

In one embodiment, at least one temperature sensor 27 is disposed at close proximity of the expandable stent 13 or a metallic member 62. Insulated temperature sensor wire means 28 passes from the temperature sensor 27, to an external temperature control mechanism 31 through the outlet connector 48. The RF energy delivery is controlled by using the measured temperature from the at least one temperature sensing means 27, through a closed-loop temperature control mechanism and/or algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

A method for supporting and ablating a vessel of a patient using an ablation apparatus system, the ablation apparatus comprises a tubular shaft having a shaft distal section, a shaft distal end, and a shaft proximal end; a handle attached to the shaft proximal end; an expandable stent disposed on the shaft distal section; and a RF current generator, wherein an electrical conductor is coupled from the RF current generator to the expandable stent for delivering RF current to said expandable stent for ablating the vessel. The method comprises the steps of (a) inserting the ablation apparatus through an artery or a vein to the location of the vessel of a patient for ablation; (b) deploying the expandable stent; and (c) applying RF current to the expandable stent to effect treatment of ablating the vessel.

The ablation apparatus system in the above-referred method may further comprise an expandable member 15 disposed between the tubular shaft 9 and the expandable stent 13, wherein a rotating member 51 extends through the tubular shaft 9 and is rotatable within the tubular shaft, and wherein a metallic member 52 is attached to the rotating member 51. In a further embodiment, the method for supporting and ablating a vessel of a patient further comprises the expandable member expanding beneath the expandable stent to enlarge a circumference of the expandable stent. The method for supporting and ablating a vessel of a patient may comprise the expandable member being an inflatable balloon.

As an alternative illustration, a method for removing an obstruction and ablating a vessel of a patient using an ablation apparatus system, the ablation apparatus comprises a tubular shaft; a hollow rotating member rotatably disposed within the tubular shaft; a metallic member disposed on an end of the hollow rotating member and forming an expandable circumferential outer surface; the expandable circumferential outer surface having a metallic contacting surface covering at least a portion of said circumferential outer surface; a movable member disposed within the hollow rotating member; the metallic member having one end coupled to said movable member and another end coupled to said hollow rotating member; an expandable member disposed beneath said metallic member for expanding the expandable metallic member into supporting engagement with the vessel; and a RF current generator, wherein an electrical conductor is coupled from the RF current generator to the metallic member for delivering RF current to said metallic member for ablating the vessel. The method comprises the steps of: (a) inserting the ablation apparatus through an artery or a vein to the location of the vessel of a patient for ablation; (b) deploying the expandable metallic member; and (c) applying RF current to the expandable metallic member to effect treatment of ablating the vessel.

The external RF current generator means has the capability to supply RF current by controlling the time, power, and temperature through an optional separate closed-loop temperature control means. The patient is connected to the RF generator means through a DIP electrode to form a closed-loop RF current system. Therefore, RF energy is applied and delivered to the targeted tissue region, through the expandable stent or metallic member of this invention. The radiofrequency energy current in this invention is preferably within the range of 50 to 2,000 kHz. The speed of the rotation of the apparatus in this invention is preferably within the range of 60 to 10,000 cycles per minute. By simultaneously applying RF energy to the electrode and by applying the rotational pressure therapy, the tissue can be treated.

In a particular embodiment, the material for the RF current delivery medium of this invention consists of conductive metals such as platinum, iridium, gold, silver, stainless steel, Nitinol, or an alloy of these metals.

From the foregoing description, it should now be appreciated that an ablation apparatus system for the tubular organs, atherosclerosis, and the treatment of vascular tissues, comprising a suitable energy source and a rotational pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation apparatus for supporting and ablating a vessel in an introduction of the ablation apparatus into the vessel, comprising:

a tubular shaft having a shaft distal section, a shaft distal end, and a shaft proximal end;

a handle attached to the shaft proximal end;

an expandable stent disposed on the shaft distal section;

an expandable member disposed between the tubular shaft and the expandable stent;

a RF current generator, wherein an electrical conductor is coupled from the RF current generator to the expandable stent for delivering RF current to said expandable stent for ablating the vessel, and wherein the RF current is within the range of 50 to 2,000 kHz; and a rotating member extending through the tubular shaft and being rotatable within the tubular shaft, wherein a helically wound metallic member is attached to the rotating member.

2. An ablation apparatus for removing an obstruction and ablating a vessel, comprising:

a tubular shaft;

a hollow rotating member rotatably disposed within the tubular shaft;

a metallic member disposed on an end of the hollow rotating member and forming an expandable circumferential outer surface;

the expandable circumferential outer surface having a metallic contacting surface covering at least a portion of said circumferential outer surface;

a movable member disposed within the hollow rotating member;

the metallic member having one end coupled to said movable member and another end coupled to said hollow rotating member;

an expandable member disposed beneath said metallic member for expanding the expandable metallic member into supporting engagement with the vessel; and a RF current generator, wherein an electrical conductor is coupled from the RF current generator to the metallic member for delivering RF current to said metallic member for ablating the vessel.

3. The ablation apparatus of claim 2, wherein the metallic member is helically wound.

4. The ablation apparatus of claim 2, wherein the expandable member is an inflatable balloon.

5. The ablation apparatus of claim 4, wherein the tubular shaft includes a fluid passageway for inflating said inflatable balloon.

6. The ablation apparatus of claim 2, wherein the metallic member is a memory coil.

7. The ablation apparatus of claim 2, wherein material for the metallic member is selected from the group consisting of platinum, iridium, gold, silver, stainless steel, Nitinol, or an alloy of their mixtures.

8. A method for removing an obstruction and ablating a vessel of a patient using an ablation apparatus, the ablation apparatus comprising: a tubular shaft; a hollow rotating member rotatably disposed within the tubular shaft; a metallic member disposed on an end of the hollow rotating member and forming an expandable circumferential outer surface; the expandable circumferential outer surface having a metallic contacting surface covering at least a portion of said circumferential outer surface; a movable member disposed within the hollow rotating member; the metallic member having one end coupled to said movable member and another end coupled to said hollow rotating member; an expandable member disposed beneath said metallic member for expanding the expandable metallic member into supporting engagement with the vessel; and a RF current generator, wherein an electrical conductor is coupled from the RF current generator to the metallic member for delivering RF current to said metallic member for ablating the vessel;

the method comprising the steps of:

(a) inserting the ablation apparatus through an artery or a vein to the location of the vessel of a patient for ablation;

(b) deploying the expandable metallic member; and (c) applying RF current to the expandable metallic member to effect treatment of ablating the vessel.

9. A method for removing an obstruction and ablating a vessel of a patient using an ablation apparatus of claim 8, wherein the expandable member is an inflatable balloon.

* * * * *